United States Patent [19]
Martone et al.

[11] 4,109,150
[45] Aug. 22, 1978

[54] SCINTILLATION CAMERA WITH THE SCINTILLATORS IN DIFFERENT PLANES

[75] Inventors: Ronald J. Martone, Cheshire; Samuel C. Goldman, Bethany; Clifford C. Heaton, Meriden, all of Conn.

[73] Assignee: Picker Corporation, Cleveland, Ohio

[21] Appl. No.: 396,762

[22] Filed: Sep. 13, 1973

Related U.S. Application Data

[62] Division of Ser. No. 121,445, Mar. 5, 1971, abandoned.

[51] Int. Cl.² ............................................... G01T 1/20
[52] U.S. Cl. ..................................... 250/368; 250/366
[58] Field of Search ......................... 250/366, 367, 368

[56] References Cited

U.S. PATENT DOCUMENTS

| 3,723,735 | 5/1973 | Spelha et al. | 250/366 |
| 3,732,419 | 5/1973 | Kulberg | 250/366 |
| 3,774,032 | 11/1973 | Lange | 250/366 |
| 3,784,819 | 1/1974 | Martone et al. | 250/366 |

Primary Examiner—Harold A. Dixon
Attorney, Agent, or Firm—Watts, Hoffmann, Fisher & Heinke

[57] ABSTRACT

A scintillation camera of the multiple phototube type. A thin light pipe and masks are employed to diffuse the light so that the camera operates on a principle of light diffusion rather than phototube "viewing" as described in the prior art.

12 Claims, 4 Drawing Figures

SCINTILLATION CAMERA WITH THE SCINTILLATORS IN DIFFERENT PLANES

CROSS REFERENCES TO RELATED PATENTS AND APPLICATIONS

This is a division, of application Ser. No. 121,445, filed Mar. 5, 1971, now U.S. Pat. No. 3,784,819 issued Jan. 8, 1974.

1. U.S. Pat. No. Re 26,014 issued May 3, 1966 to J. B. Stickney et al, a reissue of U.S. Pat. No. 3,070,695, dated Dec. 25, 1962, entitled "Scintillation Scanner".

2. Application for U.S. Pat. Ser. No. 837,072, filed June 27, 1969 by Ronald J. Martone, Peter G. Mueller and Robert Hindel, entitled "Scintillation Camera", (hereinafter the HINDEL application).

3. Application for U.S. Patent Ser. No. 833,552, filed June 16, 1969 by Ronald J. Martone, Peter G. Mueller and Richard J. Flis, entitled "Scintillation Camera", (hereinafter the MARTONE application).

BACKGROUND OF THE INVENTION

1. Field of the Invention

This invention pertains to gamma imaging devices and more particularly to that class of devices known as scintillation cameras.

In the diagnosis of certain illnesses, radioactive agents are administered to patients. These administered agents have the characteristic of localizing in certain tissues and either not localizing, or localizing to a lesser degree, in other tissues. For example, iodine 131 will localize in thyroid glands. A representation of the spatial distribution and concentration of administered iodine 131 in a thyroid gland provides an image of the gland itself which is useful in diagnosing the condition of the gland.

2. Description of the Prior Art

Generally speaking, two classes of devices known as scanners and cameras have been used to detect and represent the spatial distribution and localization of radioactive isotopes. Typically, a scanner has a scintillation probe which is moved along a plurality of spaced parallel paths. Gamma energy detected by the probe results in a display through either a photographic or a dot image representative of the spatial distribution and localization of an isotope. A clinically successful scanner is described in greater detail in the above-referenced patent Re 26,014.

The devices known as cameras remain stationary with respect to the patient as a representation of the spatial distribution of radioactivity is developed. With many of these cameras, a relatively large disc-shaped scintillation crystal is positioned to be stimulated by radiation emitted from the patient. In most cameras, a collimator is interposed between the patient and the crystal so that, for example, with a parallel hole collimator the rays striking the crystal are all generally perpendicular to it.

The crystal scintillates as it converts gamma energy impinging on it to light energy. The light is transmitted through a suitable light pipe, to an array of phototubes. When a phototube is stimulated by light generated in a crystal by a scintillation, an electrical signal is emitted which is proportional to the intensity of light energy received by that tube. When a scintillation causes all or substantially all of the phototubes to emit signals, these signals are emitted concurrently and are then summed to provide a signal known as the Z signal. This Z signal is conducted to a pulse-height analyzer to determine whether the signal reflects the occurrence of a so-called photopeak event to the isotope which has been administered to the patient. That is, the Z-signal is of appropriate strength to reflect the full conversion of the energy of a gamma ray emitted from the administered isotope to light energy by the crystal.

Summing and ratio circuits are also provided which develop what are known as X and Y signals. These X and Y signals cause a dot to be produced on the screen of the oscilloscope at a location corresponding to the location of the detected scintillation. Thus, the oscilloscope dots are displaced relatively, each at a location corresponding to the location of the corresponding scintillation in the crystal and the oscilloscope dots are integrated to produce an image. Suitable circuits for producing an oscilloscope image of spatial distribution of a radioactive isotope are described in greater detail in the HINDEL application.

The phototubes, the circuits and the oscilloscope function as a unit to provide a light amplifier such that each dot produced on the oscilloscope is a brightened representation of a scintillation. Through the use of a persistence screen on the scope, or a photographic camera, these dots are integrated to produce an image.

With cameras of the type using an array of phototubes, the literature has described a spacing of the phototubes a sufficient distance from the crystal so that the tubes "view coextensive areas". Typically, there will be a spacing of the order of two inches between a crystal and a phototube. More specifically, since the typical crystal is thallium activated sodium iodide, it is hygroscopic and must be hermetically enclosed. At the output side of the crystal, the typical hermetic enclosure includes a glass window which has a thickness of about one-half inch. A light pipe, such as the light pipe described in greater detail in the MARTONE application, is optically coupled to both the window and the phototubes. Typically, the light pipe will have a thickness of the order of one and one-half inches.

Thus, in a camera of these typical dimensions, any scintillation occurring to the crystal must, as a minimum, be at least two inches from the nearest phototube. Proposals for somewhat thinner light pipes are known, but the thinnest of these has been one and three-eighths inches, which, if coupled with a one-half inch glass, results in a minimum scintillation-to-phototube distance of one and seven-eighths inches.

It may generally be said that the further a scintillation is from the phototube, the weaker will be the light signal received by the phototube and accordingly, the weaker the electrical output of the phototube. Accordingly, the closer the phototubes are to the scintillation, the stronger will be the signals. Both theory and experiment indicate that this will better the spatial resolving power of the instrument.

As noted above, it has been taught that the tubes must be sufficiently spaced to view overlapping, coextensive areas in the scintillator. In addition, which known light pipe constructions, if the spacing between the crystal and the phototubes is too small, there is a loss of uniformity and linearity. That is, the response of the system to a uniform source of activity will exhibit bright and dark areas not related to the isotope concentration and furthermore, light signals produced on the oscilloscope will be displaced from the desired position and the result is a distorted image. Additionally, it is known there will be a loss of uniformity of system sensitivity. That is, the pictures formed by integrating light dots will exhibit light or dark areas not related to isotope concentration, this indicating a preferential ability to detect scintillations in certain parts of the crystal.

SUMMARY OF THE INVENTION

It has now been discovered that a camera constructed to operate on a principle totally different from the principle summarized above and described in greater detail in the literature, will have spatial resolving power far in excess of that theoretically obtainable in the past and far in excess of that which has heretofore been obtained in practice.

Tests have shown that bars 7/32 of an inch can consistently be resolved at 140 KeV with a camera having a 13½ inch crystal with a 12 inch field of view and 19 phototubes. With prior cameras, resolving power of the order of 12/32 of an inch bars was considered superior in a 13½ inch crystal at this energy. In an 11½ inch crystal with a 9½ inch field of view, with 19 tubes more closely packed, a resolving power of 8/32 of an inch was considered superior at 140 KeV.

Up to this point in the art, it has been generally accepted that with a 9½ inch field size and 19 phototubes, one inherently must achieve greater resolution than with a 12-inch field size and 19 identical phototubes because the phototubes are more tightly packed. With the present invention, resolution superior to that heretofore obtained has been achieved with an appearance of repeal of what has been referred to as "an immutable physcial optical law".

According to the present invention, a relatively thin light transmitter is used, i.e. a light transmitter of the order of ½ inch or less in thickness. Masks are interposed at selected locations between the phototubes and the scintillator. The masks reflect and diffuse the light so that a generalized glow is achieved throughout the light transmitter. When a mask is between the scintillator and one or more phototubes, it prevents the direct transmission of a portion of light from the point where a scintillation occurs to those phototubes.

The phototubes emit electrical signals with the strength of each signal being proportional to the intensity of diffused and direct light conducted by the light transmitter to each phototube. Electronic circuitry of the type described in the HINDEL application is then utilized to determine the locus of the diffused light and cause a dot to be produced on a read-out device at a location corresponding to the point at which a photopeak event occurred in the crystal.

In a 19-phototube scintillation camera, it is now conventional to have one center tube surrounded by an inner ring of six tubes which inner ring is, in turn, surrounded by an outer ring of 12 tubes. The tubes are so located that the axis of each tube is disposed in a plane which is perpendicular to the crystal and which includes the axis of the center tube and at least one other tube.

Outstanding results are achieved by using a mask which takes advantage of this positioning of the phototubes. Specifically, referring to the center tube, a mask is provided on the surface of the light transmitter adjacent the crystal window. This mask is of spoke-like configuration with a central hub-like portion and thin strips extending radially of phototubes. Each strip is symmetrical about a plane located by the axes of a plurality of the phototubes. The strips may be of equal length or of such length and shape as to optimize the operating parameters of the system.

The described mask, then, diminishes the quantity of light which is transmitted directly to the central phototube and also to other phototubes. At the same time, the proportion of diffused or reflected light reaching these other tubes will generally increase.

In the preferred form of the invention, seven of these hub-like patterns are provided, each being axially aligned with a different phototube. The seven hub-like masks are interposed between the crystal and the central phototube and the phototubes of the inner ring. The masks may take many forms and are most simply and preferably formed of a light-reflective tape or paint.

Small strip-like shields are provided with respect to selected ones of the phototubes in the outer ring while other of the phototubes in the outer ring are not shielded at all in the preferred embodiment. These shields are located between the phototubes and the light transmitter and their purpose is to extend the useful field of view of the device.

Accordingly, the object of the invention is to provide a novel and improved scintillation camera which functions on a principle of light diffusion and reflection rather than principles of "coextensive fields of view" as described in the prior art.

Other objects and a fuller understanding of the invention may be had by referring to the following description and claims taken in conjunction with the accompanying drawings.

DESCRIPTION OF THE PREFERRED EMBODIMENT

Figure 1:
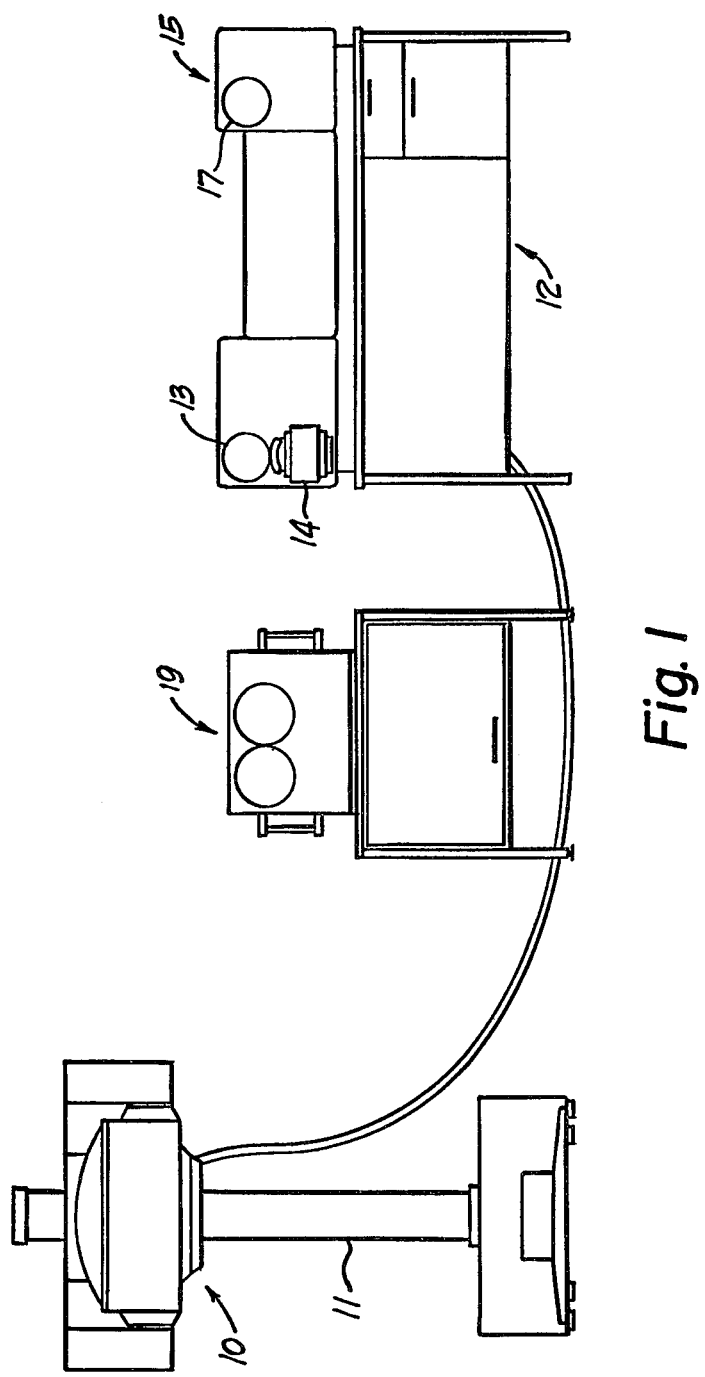
FIG. 1 is a plan view of a camera and associated consoles utilizing the novel detecting head and light transmitter of this invention.

Referring now to FIG. 1, a detector head is shown generally at 10. The head is adjustably mounted on a stand 11 for positioning adjacent a patient or other subject. Electrical signals from the head 10 are conducted to circuitry contained within a console shown generally at 12.

The signals, after processing by the circuitry, produce an image, on a monitor oscilloscope 13, of the distribution of an isotope in the subject under investigation. A duplicate image is produced on a camera oscilloscope, not shown, which is viewed and photographed by a camera 14.

The circuitry in the console 12 first produces analog signals in manners more completely described in the referenced applications. Assuming the analog signals represent photopeak events, they are digitized. The digital signals may be fed to a computer for analysis and diagnosis.

The digital information is also fed to a built-in digital data processor 15. This processor utilizes the digital information to generate either a variable width profile histogram of counts versus horizontal distance or a histogram of counts versus time. Such histograms are displayed on a monitor 17.

The digital information is also fed to a tape recording console shown generally at 19 for storage and subsequent utilization. The digital information is reconverted to analog to produce the images displayed on the monitor oscilloscope 13 and recorded by the camera 14.

Figure 2:
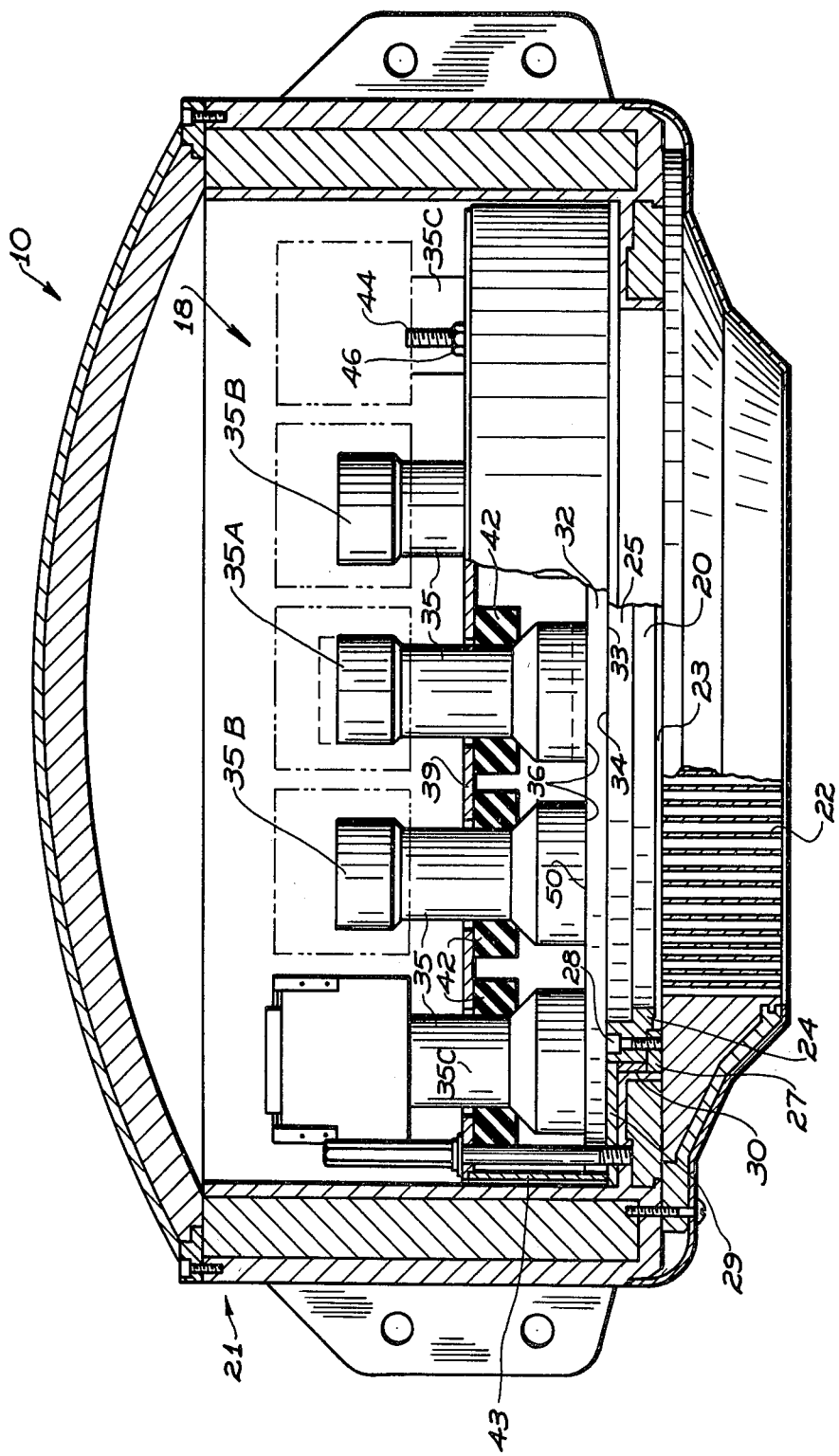
FIG. 2 is a fragmentary sectional view of the detector head of this invention.

The construction of the detector head 10, including an imaging subassembly 18, is shown in FIG. 2. The subassembly is mounted in a housing 21. The subassembly includes a large scintillation crystal 20 of thallium-activated sodium iodide. A collimator 22 shown in the form of a parallel hole type, is removably secured to the housing 21. The housing and the perimetral portions of the collimator are formed of shielding material such as lead so that essentially the only radiation which reaches the crystal has travelled along a determinable path through the collimator.

A gamma ray input window 23 is provided. The window 23 is opaque to light but substantially transparent to gamma radiation in the energy range generally used. This input window is typically an aluminum disc fixed to and hermetically sealed to a surrounding crystal supporting ring 24. A glass output window 25 is carried by the crystal supporting ring 24. The crystal 20 and the input and output windows 23, 25 and its supporting ring 24 constitute a component which is commercially available from The Harshaw Chemical Company of Cleveland, Ohio. The window component is secured to a supporting ring 27 by suitable fasteners 28. The supporting ring 27 is connected to a crystal assembly support ring 29 by an annular spacer 30.

A light transmitter 32 is provided. This light transmitter 32 is a disc of transparent material suitable for conducting the light emitted by the crystal such as ultraviolet transmitting Plexiglas. The light transmitter 32 has a planar input face 33 that is optically coupled to a polished, planar output face 34 of the output window 25.

A plurality of phototubes 35 are provided. The phototubes 35 are arranged in an array with a total of 19 such tubes being provided. The array comprises a central tube 35A, an inner ring of six tubes 35B around the central tube, and an outer ring of twelve tubes 35C. The phototubes 35 have input windows 36 which are juxtaposed against the light transmitter 32 in a manner which will be described in greater detail presently. Suitable conductors, not shown, couple the phototubes 35 to the circuitry in the console 12.

An apertured tube locator and cover plate 39 is provided. Annular bushings 42 surround a corresponding one of the phototubes. The bushings 42 are interposed between the cover plate 39 and the phototubes 35. The bushings are compressible and, on clamping of the assembly together in a manner which will be described presently, bias each of the tubes 35 into surface engagement with an appropriate portion of the light transmitter 32.

A spacer cylinder 43 and a plurality of studs 44 are provided. The studs 44 project through the cover plate 39 and are secured to the crystal assembly support ring 29. The cover plate 39 and the crystal assembly support ring 29 are clamped against the spacer cylinder 43 by tightening down suitable nuts 46 on the studs 44. This fixes the entire lift-out phototube assembly together with the phototubes 35 in closely juxtaposed relationship and good optical coupling with the light transmitter 32 and the light transmitter in turn optically coupled to the glass window 25.

Figure 3:
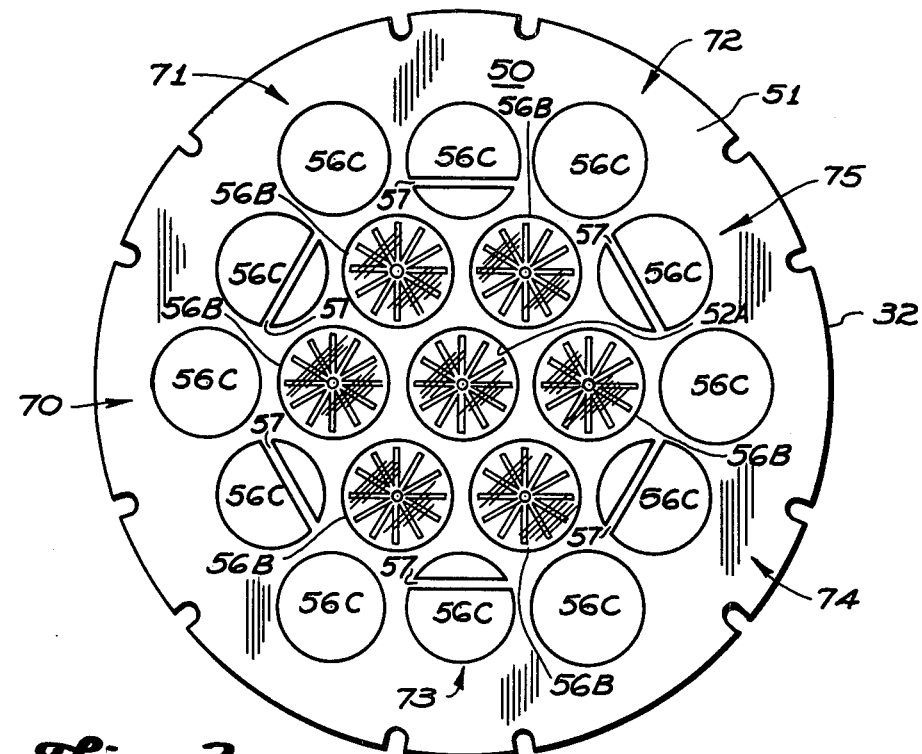
FIG. 3 is a plan view of the light transmitter of this invention as seen from the phototube side of the light transmitter; and, FIG. 4 is a plan view of the light transmitter of this invention as seen from the scintillation crystal side of the light transmitter.

FIG. 3 is a plan view of the phototube side of the light transmitter 32. As has been indicated, the light transmitter 32 is formed of a material essentially transparent to the light emitted by the scintillator. Phototube face 50 of the light transmitter 32 is painted with a reflective coating 51 over its entire surface except where the output face 50 will be optically coupled to the phototube array. Thus, there is a central opening 52A to which the central phototube is optically coupled. Six openings 56B of an inner ring are respectively optically coupled to the inner ring of phototubes, and twelve openings 56C of an outer ring are respectively coupled to the 12 phototubes in the outer ring. Thus, the entire phototube face of the light pipe, except for 19 holes, each the size of the input phosphor of a coupled phototube, is covered by a light reflective coating which contributes to the reflection and diffusion of light throughout the light pipe.

As an examination of FIG. 3 will show, six of the phototubes in the outer ring are closer to the central phototube than the remaining six phototubes. In order to increase the useful field size of the system, each phototube in the outer ring has partial shields in the form of strips 57 extending across the openings 56C in the six more-closely spaced openings. These masks may be formed in many ways as by the use of masking tape, paper, or the like; but are preferably painted strips of the same material used for the rest of the coating 51. The mask strips 57 are applied at the same time as the coating 51 so that the strips are part of the coating.

Figure 4:
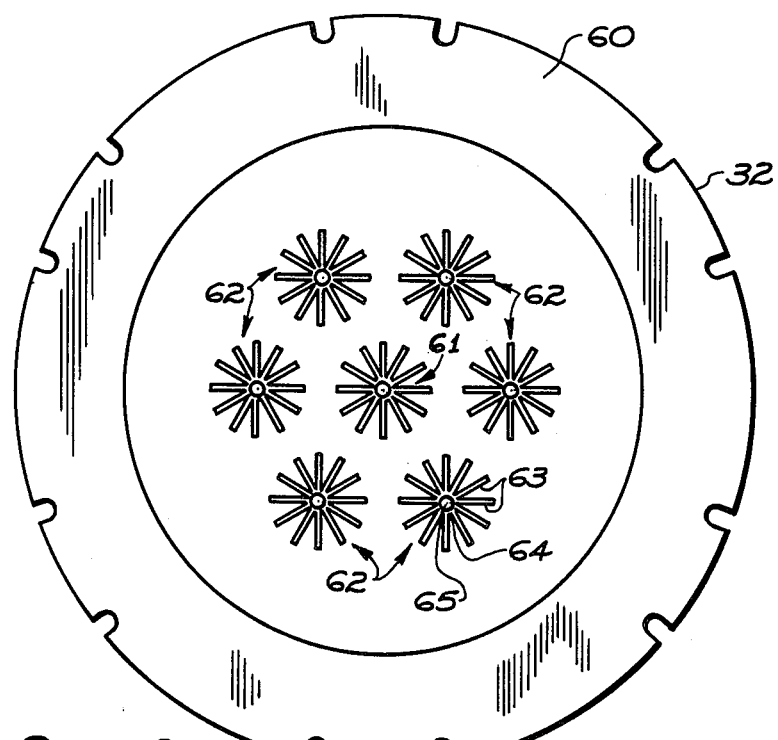

Referring now to FIG. 4, the crystal side of the light transmitter 32 has a perimetral ring 60 formed with a reflective coating preferably of the same material as used on the coating 51. The inside diameter of the ring 60 corresponds to the diameter of the window 25. Thus, the crystal side of the light transmitter in the area surrounding the window is coated with a reflective material to assist in the light diffusion while the unmasked area within the ring 60 is directly optically coupled to the window 25.

Masks for the central phototube 35A and the inner ring of phototubes 35B are shown in one form in FIG. 4. The mask for the central phototube is designated by the numeral 61 while the masks for the phototubes in the inner ring are designated by the numeral 62. Each of these masks is a spoke-like arrangement having a series of spokes 63 connected together by an annular hub-portion 64. Each mask, in its preferred and disclosed form, has an aperture 65 at the center. The masks 61 and 62 are each axially aligned with the related phototube with a central hole that is in axial alignment with the phototube and surrounding spokes and hub 63, 64 that diffuse and reflect the light. These masks preferably are also formed of the same coating material used in the coating 51 but can, like the masks 57, be formed in other ways.

An examination of FIG. 3 will make it apparent that the spokes are each located according to the geometry of the phototube array. Each spoke is disposed symmetrically about a plane located by the axis of the masked tube and the axes of other phototubes. Thus, the central tube over the aperture 52A is the central one of three rows, 70, 71, 72 of five apertures each.

Further improvement in the performance of the instrument can be achieved by spacing of the central phototube further from the crystal 20 than the remainder of the tubes as shown in phantom in FIG. 2. This is a new method to eliminate a center "hot" spot which can otherwise occur. Thus, for the first time, the tubes are not located in a common plane and improved results are achieved.

In addition to the advantages previously described, the following additional advantages have been realized with the masks:
1. Z signals are more uniform. That is, a weighted sum of the output signals of all phototubes is more uniform with respect to the lateral position of the scintillation than in prior cameras where there was an appreciable variation depending upon whether a scintillation was immediately below one of the phototubes or at a location immediately below a space not covered by a phototube.
2. The light guiding system, by redistributing scintillation light, does not depend on maximum amount of light reaching the phototubes, but rather intentionally disperses, diffuses, or scatters some of the light to provide a more uniform response of the camera to light pulses at various positions. This allows the use of a thin light transmitter and thus, more accurate spatial resolving power.
3. The use of masks makes more constant the sensitivity of the system to light pulses in the crystal. Thus, "hot" or "cold" regions in the picture which might be mistaken for subject abnormalities are reduced in size, number and intensity.
4. The technique virtually eliminates the phenomenon known as "edge effect" in which a bright ring appears in the periphery, of the crystal. In this connection, a black coating is applied to the inner surface of the spacer cylinder 43 to absorb light which escapes from the perimeter of the light transmitter 32.
5. Even though it is possible to use a light transmitter of only ½ inch thickness in a camera of the described construction, by the use of this invention, the linearity can be maintained to within plus or minus five percent of the overall image size.

Although the invention has been described in its preferred form with a certain degree of particularity, it is understood that the present disclosure of the preferred form has been made by way of example only and that numerous changes in the details of construction and the combination and arrangement of parts may be resorted to without departing from the spirit and the scope of the invention as hereinafter claimed. For example, the masking material could be an integral part of the light transmitter by way of opaquing of the generally plastic material.

What is claimed is:
1. A scintillation camera comprising:
   (a) an array of scintillation responsive devices including at least one centrally disposed scintillation responsive device surrounded by others of said scintillation responsive devices;
   (b) light emitting means for emitting flashes of light to said scintillation responsive devices in response to incident radiation stimuli; and,
   (c) certain of said scintillation responsive devices being positioned substantially within the same plane and a centrally disposed one of sqid scintillation responsive devices being positioned out of said plane.
2. The scintillation camera of claim 1 wherein said scintillation responsive devices comprise phototubes and said centrally disposed scintillation responsive device comprises a single centrally located phototube disposed further from said light emitting means than are the remainder of the phototubes.
3. The scintillation camera of claim 1 additionally including a light conductor interposed between said light emitting means and said scintillation responsive devices and defining input and output faces, said input face comprising a generally planar input surface positioned near said light emitting means, and said output face comprising a first planar surface portion adjacent said certain scintillation responsive devices and a central planar surface portion spaced from the first surface portion and adjacent said centrally disposed scintillation responsive device.
4. A method of improving the resolution of a scintillation camera of the type comprising a light emitting mechanism which emits light flashes in response to incident radiation stimuli, and an array of light responsive devices positioned in a common plane to receive the light flashes, comprising the step of repositioning the central-most one of said light responsive devices out of said plane at a greater distance from said light emitting mechanism than are the remainder of said light responsive devices.
5. In a radiation image device having a scintillator, means for emitting electrons in response to light from said scintillator, and light conductive means between the scintillator and electron emitting means, the improvement comprising means on either the light conductive means or the electron emitting means and between the scintillator and the electron emitting means for selectively attenuating the light emitted by said scintillator.
6. In a radiation image device having a scintillator, a plurality of photomultiplier tubes positioned to receive light from the scintillator, and light conductive means between the scintillator and the photomultiplier tubes, the improvement comprising means on either the light conductive means or the photomultiplier tube for selectively attenuating the light emitted by the scintillator which is received by the photomultiplier tubes.
7. The structure of claim 6 further characterized in that the means for attenuating the light received by the photomultiplier tubes includes a plurality of opaque areas positioned on a surface of the light conductive means.
8. The structure of claim 7 further characterized in that said opaque areas are positioned on that surface of the light conductive means nearest the photomultiplier tubes.
9. The structure of claim 7 further characterized in that said opaque areas are each in alignment with a photomultiplier tube.
10. The structure of claim 9 further characterized in that there is at least one opaque area in general axial alignment with each photomultiplier tube.
11. The structure of claim 10 further characterized in that each opaque area is located generally in the center of each photomultiplier tube.
12. The structure of claim 11 further characterized in that each of said opaque areas are generally the same in size and configuration.

* * * * *